United States Patent [19]

Wang et al.

[11] Patent Number: 5,034,107
[45] Date of Patent: Jul. 23, 1991

[54] METHOD FOR SENSING NITROUS OXIDE

[75] Inventors: Da Y. Wang, Lexington; Daniel T. Kennedy, Burlington; Burton W. MacAllister, Jr., Hudson, all of Mass.

[73] Assignee: GTE Laboratories Incorporated, Waltham, Mass.

[21] Appl. No.: 449,640

[22] Filed: Dec. 12, 1989

[51] Int. Cl.⁵ .......................................... G01N 27/417
[52] U.S. Cl. ............................... 204/153.14; 204/425; 204/426
[58] Field of Search ................ 204/153.14, 153.18, 204/421–429

[56] References Cited

U.S. PATENT DOCUMENTS

| | | | |
|---|---|---|---|
| 2,773,237 | 12/1956 | Offutt et al. | 204/153.1 |
| 4,450,065 | 5/1984 | Yamada et al. | 204/412 |
| 4,769,124 | 9/1988 | Okada et al. | 204/426 |
| 4,770,760 | 9/1988 | Noda et al. | 204/153.14 |
| 4,909,072 | 3/1990 | Logothetis et al. | 204/426 |

Primary Examiner—T. Tung
Attorney, Agent, or Firm—Carl F. Ruoff

[57] ABSTRACT

A method for identifying and determining the concentration of nitrous oxide in a gas containing nitrous oxide, oxygen and nitrogen is disclosed. A negative voltage is applied across a set of electrodes separated by an electrolyte wall. The voltage is of such a magnitude to produce an electric current which is on a plateau. The current is measured initially using air or oxygen as a test gas. After this reading is taken the gas containing nitrous oxide in oxygen and air is measured for its current and the concentration of nitrous oxide is determined using the two measured currents. The negative voltage can be applied at two different magnitudes to have two currents measured. Nitrous oxide containing mixtures would yield equivalent current readings.

10 Claims, 3 Drawing Sheets

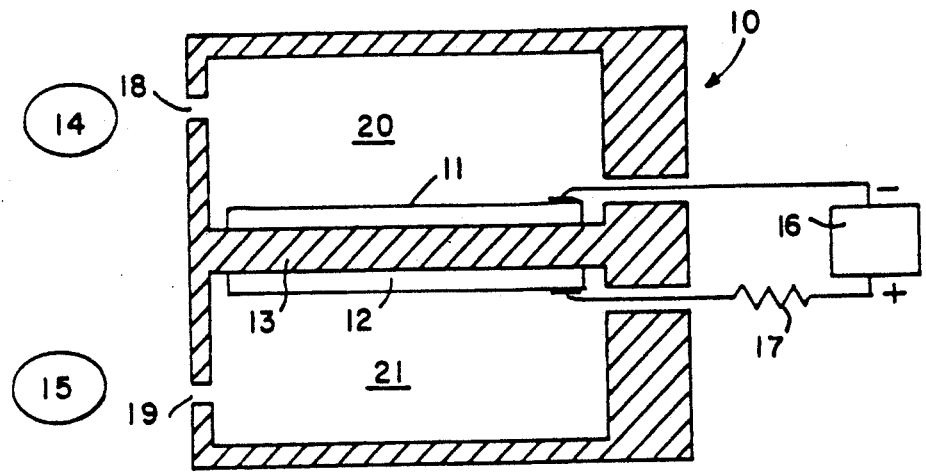
FIG. 1
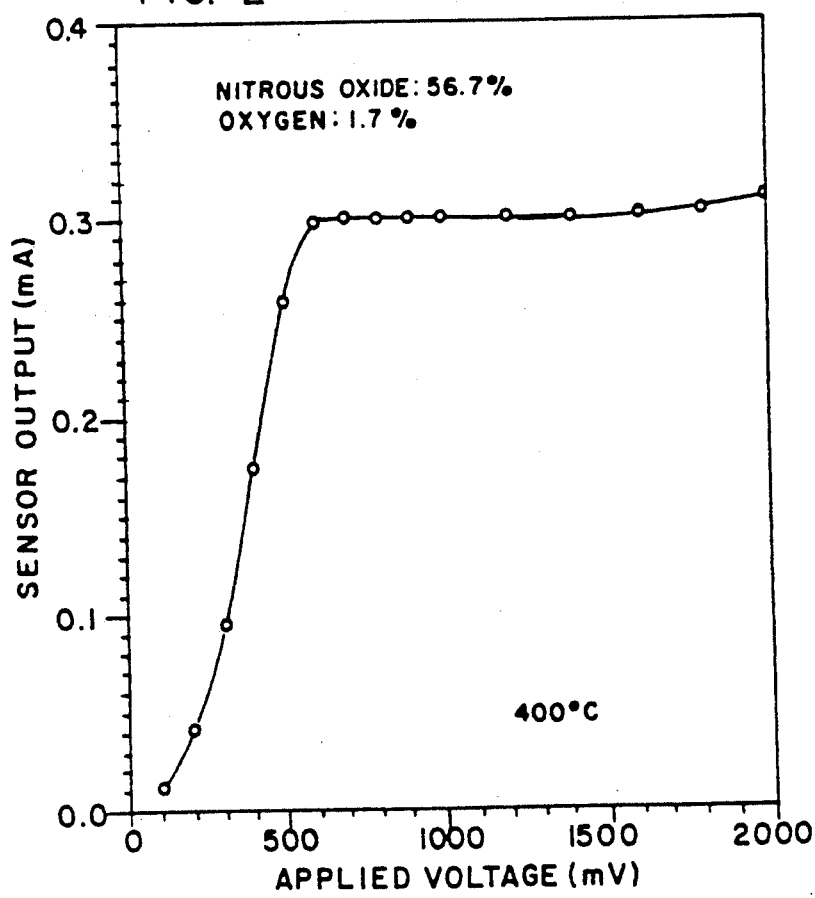

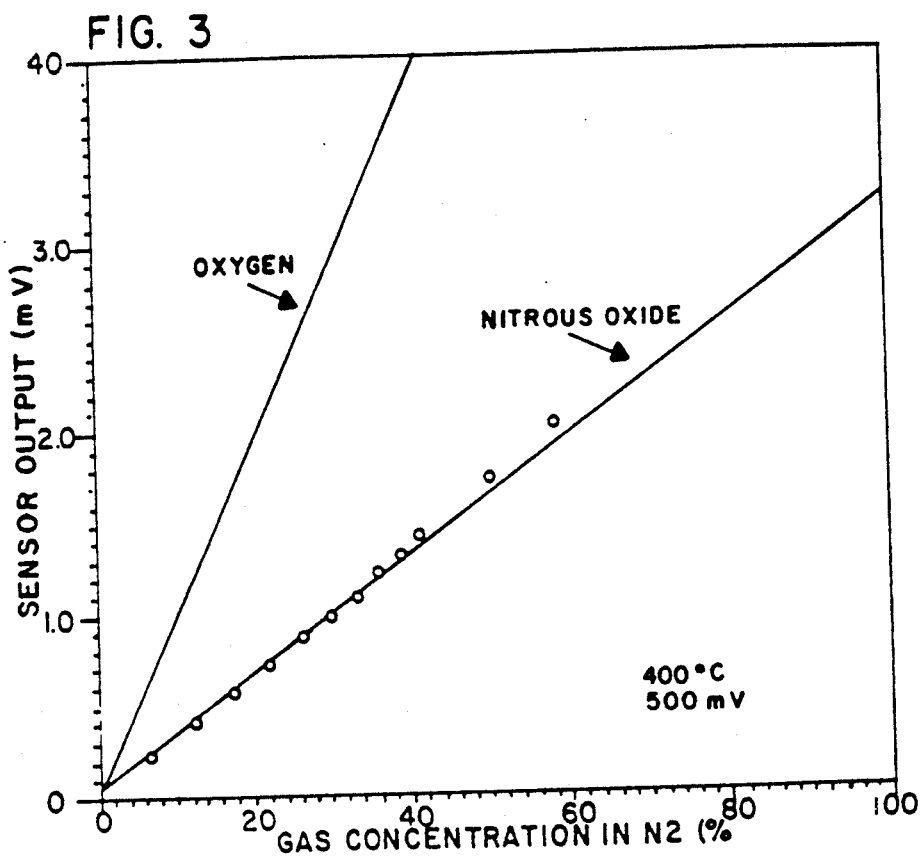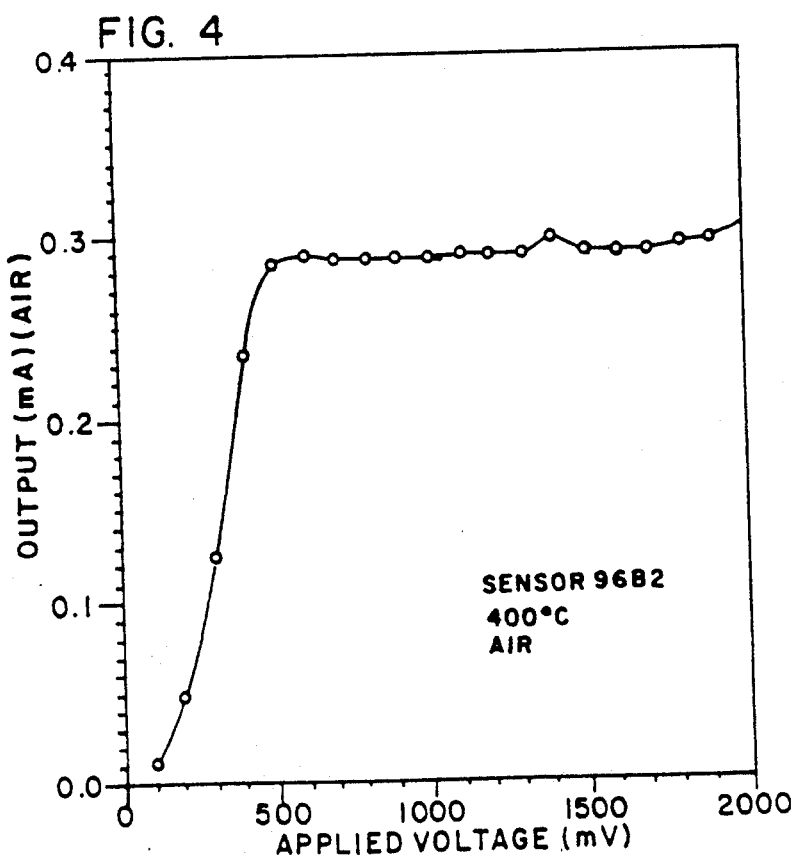

METHOD FOR SENSING NITROUS OXIDE

INCORPORATION BY REFERENCE

U.S. patent application Ser. No. 07/198,028 filed May 25, 1988, by Wang, MacAllister and Kennedy for Gas Sensing Apparatus, assigned to the same assignee as the present application, is hereby incorporated by reference.

BACKGROUND OF THE INVENTION

There are numerous methods to detect nitrous oxide gas including calorimetric, chemoluminescent and gas chromotography. However, all these methods require the use of expensive and complex equipment. This makes it impractical to perform real-time monitoring and control of nitrous oxide gas for applications such as medical anesthesia.

The present invention solves these problems by using economical components which are easy to operate and can be readily incorporated into medical anesthetic equipment to detect and control oxygen and nitrous oxide concentration simultaneously.

It has been found that the identity and concentration of a reducing or oxidizing gas species can be determined by electrochemical pumping of oxygen. If one knows the oxygen concentration of a carrier gas containing an unknown reactive species, one can determine the identity and concentration of the unknown species. This is accomplished by applying a voltage across a pair of electrodes separated by a solid electrolyte and "pumping" oxygen through the electrolyte. The voltage required to pump the oxygen is call the pumping voltage. As the oxygen is being pumped, a current flows and this current is measured. This current is called the oxygen limiting current.

It has been found that for many gas species, including methane, hydrogen and propane two oxygen limiting current plateaus are observed as the pumping voltage increases. By measuring these current plateaus one is able to determine the identity and concentration of the reactive gas. However, nitrous oxide does not exhibit this phenomenon, that is, only one current plateau is observed. However, it is possible to determine the nitrous oxide concentration and its identity in the test gas by measuring the oxygen limiting current for two different pumping voltages.

SUMMARY OF THE INVENTION

A method for detecting and determining the concentration of nitrous oxide in a nitrous oxide, oxygen and nitrogen gas mixture is described. A solid electrolyte sensor having a solid electrolyte wall in contact with and interposed between a first and a second electrode is provided with the first and second electrodes being exposed to a test gas containing a known amount of oxygen. A first negative voltage is applied across said first and second electrodes, causing electrochemical pumping and first electric current to flow through the electrolyte wall, said first negative voltage of a magnitude to cause said first electric current to be on a current plateau. The magnitude of the first electric current is measured. The test gas is removed and replaced with a gas containing nitrous oxide, oxygen and nitrogen. A second negative voltage is applied across said first and second electrodes causing electrochemical pumping and a second electric current to flow through the electrolyte wall, said negative voltage of a magnitude to cause said second electric current to be on a current plateau. The magnitude of said second electric current is measured.

The concentration of nitrous oxide in the test atmosphere is determined by comparing the magnitude of the first and second electric currents.

In an alternate embodiment, a third negative voltage is applied across the first and second electrode which causes electrochemical oxygen pumping and a third electric current to flow through the electrolyte wall. If the third negative voltage is substantially greater than the second negative voltage and the second and third currents are identical it can be concluded that nitrous oxide is the unknown reactive species contained in the gas.

BRIEF DESCRIPTION OF THE DRAWING

FIG. 1 shows a cross-sectional view of the nitrous oxide sensor.

FIG. 2 shows a polargraphic plot of applied voltage versus measured current for a nitrous oxide, oxygen, nitrogen gas mixture at 400° C.

FIG. 3 shows a plot of the measured current plateau versus nitrous oxide concentration in nitrogen and oxygen concentration in nitrogen at 400° C.

FIG. 4 shows a polargraphic plot of the applied voltage versus measured current for air at 400° C.

DETAILED DESCRIPTION OF THE PREFERRED EMBODIMENTS

Figure 5:
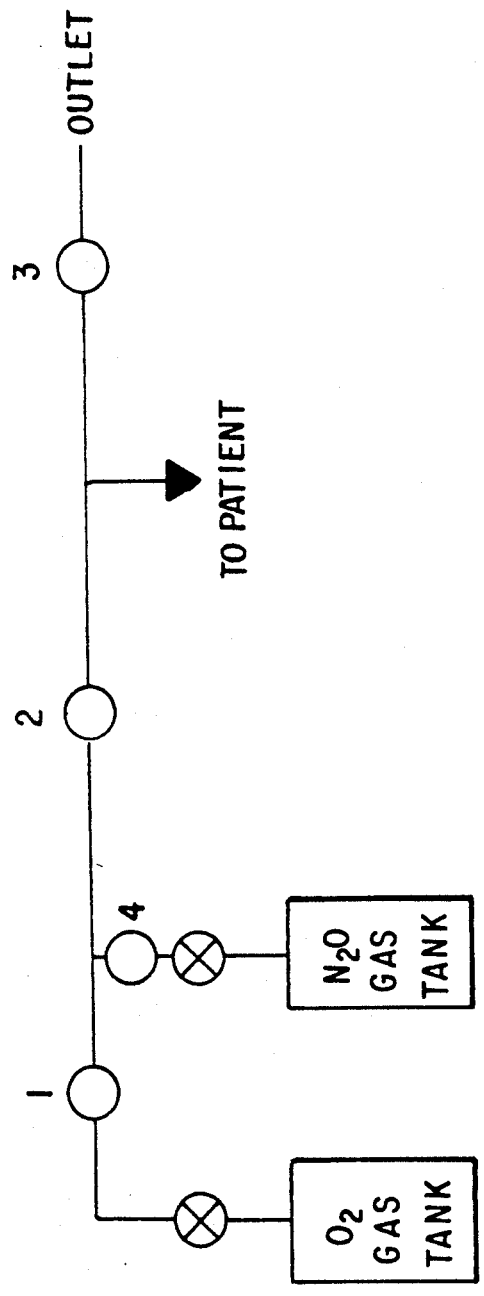
FIG. 5 shows an application for the nitrous oxide sensor described in FIG. 1.

The present invention discloses a method and apparatus for determining nitrous oxide gas concentration in a gas stream. The equipment required is simple to operate and easy to install.

A layout of the nitrous oxide sensor is shown in FIG. 1. The main body 10 of the device is made of 6-8 mole percent yttria stabilized zirconia. Other oxygen-anion conducting materials can be used such as ceria doped with calcia or yttria. The sensor has two partially enclosed chambers 20 and 21 where gas containing the nitrous oxide can diffuse in and out of the chambers 20, 21 through the two small orifices 18, 19. Two platinum electrodes 11 and 12 are screen printed on partition wall 13 which separates the two chambers 20, 21. To detect and measure the nitrous gas concentration, a constant DC voltage is applied to the electrodes 11, 12 by power source 16. The voltage applied is less than the dissociation energy of the electrolyte. For zirconia this value is approximately 2400mV. The current produced is determined by measuring the voltage drop across resistor 17.

Shown in FIG. 2 is a plot of applied voltage versus current output for a gas mixture containing 56.7% nitrous oxide, 1.7% oxygen and the remainder being nitrogen tested at 400° C. This graph shows the limiting current that occurs. The plateau shown in FIG. 2 gives the limiting current. For other reducing gases (such as hydrogen, methane) or oxidizing gases (such as $H_2O$), two plateaus with different limiting currents occurs. This difference offers a means to identify nitrous oxide in the gas mixture.

FIG. 3 shows the limiting current plotted against nitrous oxide concentration in nitrogen at 400° C. As shown by FIG. 3, this relationship between current and nitrous oxide concentration is linear throughout the conditions measured. This relationship allows one to determine nitrous oxide concentration in a gas mixture containing nitrogen and nitrous oxide. FIG. 3 shows a similar relationship for oxygen.

The device shown in FIG. 1 is also capable of detecting oxygen content in air. FIG. 4 shows a typical example in which sensor current is plotted against applied voltage for air at 400° C. The plateau current shows the limiting current of oxygen gas. FIG. 4 is similar to FIG. 2 in terms of plateau current.

Referring to FIGS. 2 and 4, both gas mixtures register the same current plateau. Since air is approximately 21 (20.94) percent oxygen in composition then 19.3 percent oxygen yields the same signal as 56.7 percent nitrous oxide if the sensors are operated under equivalent conditions. From this it can be determined that the signal output of nitrous gas is 0.340 (19.3/56.7) that of oxygen. (This ratio is a weak function of the temperature, the ratio at temperature other than 400° C. can be experimentally determined).

Using this relationship, we can determine the concentration of nitrous oxide in an air gas mixture. Assuming we have a gas mixture which is composed of nitrous oxide and air which is 21% oxygen and 79% nitrogen, the sensor output will be composed of an additive signal from nitrous oxide and oxygen. Assuming X is concentration of nitrous oxide, then 1-X is the concentration of air. This leads to the following equation:

sensor output = (sensor output in air)[1 − X] +

$$\frac{.34\ X\ (\text{sensor output in air})}{.2094}$$

or $$\text{sensor output} = (\text{sensor output in air}) \cdot \left[1 - X + \frac{.34X}{.2094}\right]$$

$$\text{sensor output} = (\text{sensor output in air}) \left[1 + \frac{.1306}{.2094}\right]$$

$$\text{sensor output} = (\text{sensor output in air}) \left[1 + \frac{.1306}{.2094} X\right]$$

This yields $$X = 1.60 \left[\frac{\text{sensor output}}{\text{sensor output in air}} - 1\right] \quad (1)$$

Standard electronic means can be utilized in processing the signal output from the device to display the gas composition of nitrous oxide and air.

In a similar derivation, if oxygen and nitrous gas are the only species present in the gas stream, one can measure the current produced from a pure oxygen sample and from this determine the percentage of nitrous oxide in a nitrous oxide, oxygen gas mixture. Assuming X is the concentration of nitrous oxide in the gas stream, then 1-X is the concentration of oxygen in the gas stream. This leads to the following equation:

Sensor output = (sensor output in oxygen)(1 − X) +

.34X(Sensor output in oxygen)

$$\frac{(\text{sensor output})}{(\text{sensor output in oxygen})} = (1 - X) + .34X$$

or $$\frac{\text{sensor output}}{\text{sensor output in oxygen}} = (1 - .66X)$$

or $$X = 1.5 \left(\frac{\text{sensor output}}{\text{sensor output in oxygen)}}\right) \quad (2)$$

Thus, the nitrous oxide concentration can be determined.

An application for this invention is for anesthesia gas control. The typical gas mixture used in this application is three parts of nitrous oxide and one part of oxygen. Using the equations derived previously the apparatus of FIG. 1 can be used to monitor gas composition of an anesthetic agent (nitrous oxide) and its output can be used as a feedback signal for gas composition control. Such a setup is shown in FIG. 5. The process for controlling the flow of nitrous oxide is described below.

A sensor of the type described in FIG. 1 is attached at flow position 2 or 3 and a voltage of 500mV is applied. The sensor is operated at 400° C. Pure oxygen is directed through the sensor and a reading is taken. This reading can be normalized to 100. When proper oxygen flow is established, the flow of nitrous oxide is commenced. When the sensor read 50.5 as normalized against oxygen, three fourths of the flow is nitrous oxide as determined by equation 2. If the reading is 100, only oxygen is being received. If the reading is 34, only nitrous oxide is being received. If this happens, corrective measures should be taken. Once the correct mixture has been established, the patient can be anesthetized and the sensor should be continually monitored. Furthermore, the individual tanks of oxygen and nitrous oxide can be monitored individually to avoid any accident mix-up in the type of tanks. Sensors in position 1 and 4 should give 100 and 34 normalized units when both sensor outputs are normalized to a pure oxygen sample. Any deviation from these values would indicate a tank mix-up. Sensors 1 to 4 can be connected to the actuators which operate the gas values to properly adjust the gas flows. Another way to check the gas tank is to apply a negative voltage of 1800 mV to the sensor at position 2, 3 or 4, if the measured current is different from that measured at 500 mV. the tank is wrong. Although this example uses the sensor at 400° C., lower or higher temperatures are possible.

The foregoing description has been set forth to illustrate the invention and is not intended to be limiting. Since modifications and alterations of the described embodiments incorporating the spirit and substance of the invention may occur to those skilled in the art, such modifications and alterations are intended to fall within the scope of the appended claims.

What is claimed is:

1. A method for determining the concentration of nitrous oxide in a nitrous oxide, oxygen and nitrogen gas comprising:

providing a solid electrolyte sensor having a solid electrolyte wall in contact with and interposed between a first platinum electrode and a second platinum electrode said first and second platinum electrodes exposed to a test gas containing a known amount of oxygen;

applying a first negative voltage across said first and second electrodes, causing electrochemical pumping and a first electric current to flow through the electrolyte wall, said negative voltage of a magnitude to cause said first electric current to be on a current plateau;

measuring the magnitude of said first electric current;

removing the test gas and replacing it with a gas containing nitrous oxide, oxygen and nitrogen;

applying a second negative voltage of the same magnitude as the first negative voltage across said first and a second electrodes causing electrochemical pumping and second electric current to flow through the electrolyte wall, said negative voltage of a magnitude to cause said second electric current to be on a current plateau;

measuring the magnitude of said second electric current;

determining the concentration of nitrous oxide and oxygen by comparing the magnitude of said first and second electric currents.

2. The method according to claim 1 wherein said test gas is air.

3. The method according to claim 1 wherein said electrolyte wall is made of yttria stabilized zirconia.

4. A method for determining the concentration of nitrous oxide in a nitrous oxide and oxygen gas comprising:

providing a solid electrolyte sensor having a solid wall in contact with and interposed between a first platinum electrode and second platinum electrode in communication with a test gas of pure oxygen;

applying a first negative voltage across said first and second platinum electrodes, causing electrochemical oxygen pumping and a first electric current to flow through the electrolyte wall, said negative voltage of a magnitude to cause said first electric current to be on a current plateau;

measuring the magnitude of said first electric current;

removing the test gas of pure oxygen and replacing it with a gas containing nitrous oxide and oxygen;

applying a second negative voltage of the same magnitude as the first across said first and second electrodes causing electrochemical pumping and a second electric current to flow through the electrolyte wall, said negative voltage of a magnitude to cause said second electric current to be on a current plateau;

measuring the magnitude of said current;

determining the concentration of nitrous oxide and oxygen by correlating the magnitude of said first and second electric currents.

5. The method according to claim 4 wherein said electrolyte wall is made of yttria stabilized zirconia.

6. A method for detecting and determining the concentration of nitrous oxide in a nitrous oxide, oxygen and nitrogen gas comprising:

providing a solid electrolyte sensor having a solid electrolyte wall in contact with and interposed between a first platinum electrode and a second platinum electrode said first and second platinum electrodes exposed to a test gas containing a known amount of oxygen;

applying a first negative voltage across said first and second electrodes, causing electrochemical pumping and a first electric current to flow through the electrolyte wall, said negative voltage of a magnitude to cause said first electric current to be on a current plateau;

measuring the magnitude of said first electric current;

removing the test gas and replacing it with a gas containing nitrous oxide, oxygen and nitrogen;

applying a second negative voltage of the same magnitude as the first negative voltage across said first and second electrodes causing electrochemical pumping and a second electric current to flow through the electrolyte wall, said negative voltage of a magnitude to cause said second electric current to be on a current plateau;

measuring the magnitude of said second electric current;

applying a third negative voltage of a magnitude at least 1000 mV different from the first and second negative voltages across said first and second electrodes causing electrochemical pumping and a third electric current to flow through the electrolyte wall, said negative voltage of a magnitude to cause said third electric current to be on a current plateau;

measuring the magnitude of said third electric current;

comparing it with said second electric currents will be equal if nitrous oxide is the only other gas present and said third and second electric currents will be different if a gas other than nitrous oxide, oxygen and nitrogen is present; and determining the concentration of nitrous oxide and oxygen by comparing the magnitude of said first and second electric currents.

7. The method according to claim 6 wherein said test gas is air.

8. The method according to claim 6 wherein said electrolyte wall is made of yttria stabilized zirconia.

9. A method for detecting and determining the concentration of nitrous oxide in a nitrous oxide and oxygen gas comprising:

providing a solid electrolyte sensor having a solid wall in contact with and interposed between a first platinum electrode and second platinum electrode in communication with a test gas of pure oxygen;

applying a first negative voltage across said first and second platinum electrodes, causing electrochemical oxygen pumping and a first electric current to flow through the electrolyte wall, said first negative voltage of a magnitude to cause said first electric current to be on a current plateau;

measuring the magnitude of said first electric current;

removing the test gas of pure oxygen and replacing it with a gas containing nitrous oxide and oxygen;

applying a second negative voltage of the same magnitude as the first negative voltage across said first and second electrodes causing electrochemical pumping and a second electric current to flow through the electrolyte wall, said second negative voltage of a magnitude to cause said second electric current to be on a current plateau;

measuring the magnitude of said current;

applying a third negative voltage of a magnitude at least 1000 mV different from the first and second negative voltages across said first and second electrodes causing electrochemical pumping and a third electric current to flow through the electrolyte wall, said negative voltage of a magnitude to cause said third current electric current to be on a current plateau;

measuring the magnitude of said third current;

comparing said second and third electric currents, wherein said second and third electric currents will be equal if nitrous oxide is the only other gas present and said second and third electric current will be different if a gas other than nitrous oxide, oxygen and nitrogen is present; and determining the concentration of nitrous oxide and oxygen by correlating the magnitude of said first and second electric currents.

10. The method according to claim 9 wherein said electrolyte wall is made of yttria stabilized zirconia.

* * * * *